United States Patent [19]
Kelly

[11] Patent Number: 5,980,477
[45] Date of Patent: *Nov. 9, 1999

[54] GENITAL LUBRICANTS WITH ZINC SALTS AS ANTI-VIRAL ADDITIVES

[75] Inventor: Patrick D. Kelly, Glendale, Mo.

[73] Assignees: Patrick Kelly, St. Louis, Mo.; Marc Golden, New York, N.Y.

[ * ] Notice: This patent is subject to a terminal disclaimer.

[21] Appl. No.: 09/122,595

[22] Filed: Jul. 25, 1998

Related U.S. Application Data

[63] Continuation-in-part of application No. 08/464,273, Jun. 5, 1995, Pat. No. 5,785,054, which is a continuation-in-part of application No. 08/057,001, May 3, 1993, Pat. No. 5,482,053, which is a continuation-in-part of application No. 08/361,967, Dec. 22, 1994, Pat. No. 5,599,551, which is a continuation-in-part of application No. 08/056,480, May 3, 1993, abandoned, said application No. 08/057,001, and application No. 08/056,480, which is a continuation-in-part of application No. 07/737,169, Jul. 29, 1991, Pat. No. 5,208,031.

[51] Int. Cl.$^6$ ..................................................... A61F 13/00
[52] U.S. Cl. ........................... 602/77; 128/844; 128/842; 602/60; 435/240
[58] Field of Search .................................. 128/842, 844; 435/240; 602/77, 63, 75, 60

[56] References Cited

U.S. PATENT DOCUMENTS

| | | |
|---|---|---|
| 4,465,666 | 8/1984 | Lukas et al. . |
| 4,503,070 | 3/1985 | Eby . |

(List continued on next page.)

FOREIGN PATENT DOCUMENTS

| | | |
|---|---|---|
| 0 402 078 | 12/1990 | European Pat. Off. . |
| 0 514 553 | 11/1992 | European Pat. Off. . |
| 0 564 307 | 10/1993 | European Pat. Off. . |
| 2217602 | 11/1989 | United Kingdom . |

OTHER PUBLICATIONS

Chvapil, M., et al., "Reaction of vaginal tissue of rabbit and of cheek pouch of hamster to inserted collagen sponges treated with either zinc or copper," *Am. J. Obstet. Gynecol.* 130: 63–70 (1978).

Chvapil, M., et al., "Ultrastructure of the vaginal tissue of rabbits treated with collagen sponge alone and medicated with zinc and copper salts and copper wire," *Fertility and Sterility 30*: 461–469 (1978).

W.L. Williams, "New antifertility agents active in the rabbit vaginal contraception method," *Contraception 22* : 659–672 (1980).

*Primary Examiner*—Aaron J. Lewis
*Assistant Examiner*—Kelvin Hart
*Attorney, Agent, or Firm*—Patrick D. Kelly

[57] ABSTRACT

This invention relates to the use of water-soluble zinc salts as anti-viral agents in genital lubricants (such as condom lubricants or stand-alone gels), to reduce the risk of infection by sexually transmitted viruses. Such zinc-containing anti-viral lubricants can be spread on the shaft of the penis or inside the vagina before sexual intercourse, or applied in other suitable manners that causes the lubricant fluid to be coated on one or more genital surfaces during intercourse. These lubricants also can be sealed in watertight packages containing lubricated condoms, or packaged and sold as "stand-alone" lubricants in watertight containers without condoms. Preferred lubricants contain a water-soluble lubricating agent, such as glycerin or polyethylene glycol, and a suitable zinc salt, and water, to promote ionization of the salt and release of zinc ions ($Zn^{++}$). Such lubricants may also contain a thickening or suspending agent, such as a cellulose derivative, a natural gum compound, or a hydrophilic polymer, to provide a gel. Suitable zinc salts include water-soluble organic salts having relatively low molecular weights (including zinc acetate, butyrate, gluconate, glycerate, glycolate, lactate, propionate, etc.). Highly ionizing inorganic salts, such as zinc chloride or sulfate, can also be used in some formulations. Several preferred salts were tested by human volunteers, during intercourse, and did not cause any detectable irritation.

11 Claims, 3 Drawing Sheets

U.S. PATENT DOCUMENTS

| | | | |
|---|---|---|---|
| 4,816,254 | 3/1989 | Moss . | |
| 5,208,031 | 5/1993 | Kelly | 424/412 |
| 5,299,581 | 4/1994 | Donnell et al. . | |
| 5,409,905 | 4/1995 | Eby . | |
| 5,482,053 | 1/1996 | Kelly | 128/844 |
| 5,785,054 | 7/1998 | Kelly | 128/842 |

GENITAL LUBRICANTS WITH ZINC SALTS AS ANTI-VIRAL ADDITIVES

RELATED APPLICATIONS

This is a continuation-in-part of copending U.S. application Ser. No. 08/464,273, filed Jun. 5, 1995, now U.S. Pat. No. 5,785,054, which was a continuation-in-part of U.S. application Ser. No. 08/057,001, filed May 3, 1993 (issued as U.S. Pat. No. 5,482,053 on Jan. 9, 1996) and of U.S. application Ser. No. 08/361,967, filed Dec. 22, 1994 (issued as U.S. Pat. No. 5,599,551 on Feb. 4, 1997), which was a continuation-in-part of U.S. application Ser. No. 08/056,480, also filed May 3, 1993 but subsequently abandoned. Application Ser. No.08/057,001 and application Ser. No. 08/056,480 both were continuations-in-part of U.S. application Ser. No. 07/737,169, filed on Jul. 29, 1991, which issued as U.S. Pat. No. 5,208,031 on May 4, 1993.

BACKGROUND OF THE INVENTION

This invention is in the fields of biochemistry, pharmacology, and anti-viral agents. It relates to the use of zinc salts in lubricants used during sexual intercourse, to reduce the risk of infection by sexually transmitted diseases such as AIDS or genital herpes.

The background information of interest herein is discussed in a series of five U.S. patents that have already been issued, designating Patrick Kelly (the inventor herein) as sole inventor. Those five U.S. patents are U.S. Pat. No. 5,208,031 (issued May 4, 1993, claiming gel-type genital lubricants with anti-viral zinc salts, in certain types of useful packagings); U.S. Pat. No. 5,482,053 (issued Jan. 9, 1996, claiming condoms that are prepackaged with lubricants containing anti-viral zinc salts); U.S. Pat. No. 5,545,673 (issued Aug. 13, 1996, with method claims); U.S. Pat. No. 5,599,551 (issued Feb. 4, 1997, claiming gel-type lubricants in additional types of packaging); and U.S. Pat. No. 5,624,675 (issued Apr. 29, 1997, with claims directed specifically at the human immunodeficiency virus, HIV, the causative agent for AIDS). The disclosures of these five issued patents are incorporated herein by reference. Briefly, the above-cited patents all relate to the use of water-soluble salts of zinc (such as zinc acetate, lactate, gluconate, etc.) as anti-viral additives in topical genital lubricants (this term includes condom lubricants).

One object of this invention is to disclose that genital lubricants containing a water-soluble salt of zinc offer anti-viral protection, when incorporated into genital lubricant formulations that are applied topically to one or more genital surfaces during sexual intercourse. These lubricants are useful for reducing the risk of viral infection from a sexual partner.

Another object of this invention is to disclose that water-soluble salts of zinc offer anti-viral protection, when incorporated into genital lubricant formulations that also may contain a potentially irritating or semi-toxic compound, such as a spermicide or microbicide.

Another object of this invention is to disclose genital lubricants containing two or more active agents in addition to a carrier fluid. One active agent is a water-soluble anti-viral zinc salt. The second active agent is a spermicide (such as nonoxynol or other suitable surfactant), microbicide, or other active agent.

Another object of this invention is to disclose that certain water-soluble inorganic salts of zinc, such as zinc chloride and/or zinc sulfate, can offer anti-viral protection in genital lubricant formulations.

Another object of this invention is to disclose an article of manufacture comprising a condom which is enclosed within a watertight package with a hydrophilic lubricant containing a water-soluble zinc salt at a concentration that reduces the risk that a person will become infected by a sexually transmitted virus such as herpes or HIV.

SUMMARY OF THE INVENTION

This invention relates to the use of water-soluble zinc salts as anti-viral agents in genital lubricants (such as condom lubricants or stand-alone gels). Such zinc-containing anti-viral lubricants can be spread on the shaft of the penis or inside the vagina before sexual intercourse, or applied in other suitable manners that causes the lubricant fluid to be coated on one or more genital surfaces during intercourse. Such zinc-containing anti-viral lubricants also can be coated onto condoms during manufacture and enclosed in sealed watertight packages containing the lubricated condoms, or packaged and sold as "stand-alone" lubricants in watertight containers without condoms. Preferred lubricants contain at least one water-soluble lubricating agent, such as glycerin or polyethylene glycol, and a suitable zinc salt, as well as some quantity of water to promote ionization of the salt and release of zinc ions ($Zn^{++}$). If water is used, such lubricants may also contain a thickening or suspending agent, such as a cellulose derivative, a natural gum compound, or a hydrophilic polymer, to provide a gel; alternately, the carrier may be a different type of water-containing formulation, such as a cream, emulsion, or ointment. Suitable zinc salts include water-soluble organic salts having relatively low molecular weights (including zinc acetate, butyrate, gluconate, glycerate, glycolate, lactate, propionate, etc.). Highly ionizing inorganic salts, such as zinc chloride or sulfate, can also be used in some formulations. Preferred salts are those which cause no detectable irritation. The zinc-containing lubricants described herein are intended to reduce the risk of infection by a sexually transmitted pathogen, in a user who may be at risk.

DESCRIPTION OF PREFERRED EMBODIMENTS

Figure 1:
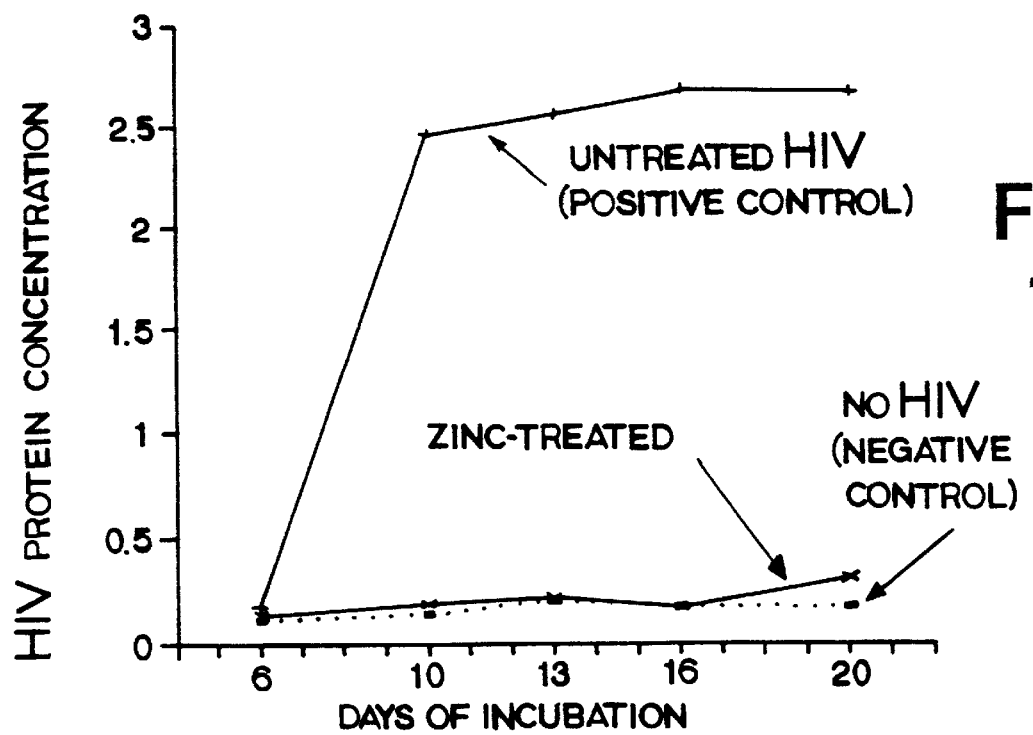
FIG. 1 shows that HIV infectivity was completely eliminated when concentrated viral stocks were incubated with 1% zinc acetate for 2 hours before the zinc-virus solution was diluted (1:30) and mixed with susceptible lymphocytes.

This invention relates to genital lubricants that are topically spread across one or more genital surfaces during sexual intercourse. Such lubricants can be used by someone who is not infected by a sexually transmitted virus (such as herpes or HIV), to decrease the risk of infection.

One method of applying a zinc-containing anti-viral lubricant to the genitals, for the purposes disclosed herein, involves removing a small quantity (such as a teaspoon, or several milliliters) of a gel, cream, ointment, emulsion, or similar formulation from a plastic or metallic tube, jar, or similar container, or from a sealed plastic, metallic or other packet containing a single dose of such lubricant, and spreading the lubricant across the surface of the penis immediately before intercourse. Alternate methods of emplacement include: (1) spreading the gel upon accessible surfaces inside the vagina shortly before intercourse; and (2) emplacing a condom, diaphragm, or similar device, which has already been coated or otherwise contacted with a zinc-containing lubricant, upon the penis or inside the vagina.

In a preferred embodiment, any of these methods of spreading a zinc-containing lubricant across the surfaces of the genitals causes the lubricant to coat and remain in contact with the genital surfaces throughout intercourse. During and after intercourse, the zinc salt dissolved in the lubricant acts as an anti-viral agent, like a chemical barrier at the site of transmission, to reduce the risk that a user will become infected by a sexually transmitted virus if a sexual partner is infected.

Preferably, such lubricants should be used in conjunction with condoms, to enhance the risk-reducing effectiveness of condoms and provide maximum protection for users. Such an increase in the anti-viral protection offered by a condom becomes important in various situations, such as when a condom breaks, or if the male loses his erection prior to withdrawal and spillage or leakage of fluid occurs from inside a condom into the vagina. The lubricant fluid can either be coated onto condoms during manufacture, and enclosed within conventional watertight plastic or foil packages that contain one condom per package, or it can be manually applied by a user to either the inside or the outside of a condom, immediately before use.

As used herein, "condom" refers to a barrier device which is used to provide a watertight physical barrier between male and female genitalia during sexual intercourse, and which is removed after intercourse. This term includes conventional condoms which cover the penis; it also includes so-called "female condoms" which are inserted into the vaginal cavity prior to intercourse. The term "condom" does not include diaphragms, cervical caps, or other barrier devices which cover only a portion of the epithelial membranes inside the vaginal cavity. Preferably, condoms should be made of latex or a synthetic plastic material such as polyurethane, since these provide a high degree of protection against viruses.

Although aqueous gel formulations (described in more detail below) are preferred for "stand-alone" lubricants that are not packaged with condoms, zinc-containing lubricants that are packaged with condoms do not require gels. A lubricant packaged with a condom requires only a water-soluble lubricating agent, such as glycerin or propylene glycol, along with a suitable zinc salt. Other components, such as water and a thickening agent, may be added to a condom lubricant if desired.

As used herein, terms such as "genital lubricant" and "topical use" refer to something that is applied to and spread across the surface of the skin or a mucous membrane (by contrast, "systemic" administration refers to a drug or other compound that is ingested orally or injected beneath the skin). A condom lubricant or other genital lubricant is a topical agent as that term is used herein.

The lubricants disclosed herein are able to reduce the risk of viral infection among users, regardless of whether these lubricants are non-irritating. As used herein, the term "non-irritating" refers to formulations that cause no noticeable irritation, or acceptably low levels of irritation, in at least some users. As disclosed elsewhere herein, the zinc salts which are preferred for use in genital lubricants are those salts which generate no detectable irritation, in at least some users.

ANTI-VIRAL MOLECULAR MECHANISMS

Although the efficacy and practical use of this invention do not depend on a specific molecular mechanism, and without tying or limiting this invention to any particular theory of action either here or elsewhere in this specification, the Applicant states that the means by which zinc salts inhibit herpes viruses (as well as HIV and, presumably, various other types of sexually transmitted viruses as well, such as hepatitis and papilloma viruses) involves at least two contributing mechanisms or factors.

Both of these molecular mechanisms involve the binding of free zinc ions, which are positively charged divalent ions ($Zn^{++}$), to negatively charged "unshared electron pairs" on certain types of amino acid residues (mainly cysteine and histidine) in proteins. This type of zinc-mediated crosslinking is extremely important to numerous types of enzymes and other proteins. In particular, it creates and stabilizes the "finger domains" in zinc finger proteins, which carry out crucial interactions with chromosomal DNA in the nucleus of every living cell on earth. These finger domains are quite stable, which indicates that zinc-mediated crosslinking bonds are quite stable.

By an analogous process, free $Zn^{++}$ ions settle into negatively-charged protein sites (also called binding sites, attachment sites, docking sites, etc.) in the "surface proteins" that are present and exposed on the surfaces of viruses. These viral surface proteins are essential to a virus's ability to bind to and infect mammalian cells; a viral surface protein normally binds to a complementary mammalian cell surface protein in a highly selective and highly specific manner, comparable to an antigen-antibody binding reaction. This binding reaction requires that positively-charged and negatively-charged sites in both sets of proteins (i.e., in a viral surface protein and a cell surface protein) line up in a manner that causes and allows the two proteins to fit together in a relatively tight and secure binding reaction. This type of reaction has often been analogized to a "lock and key" arrangement; only keys having a certain size and shape fit a certain specific lock. This requirement for complementarity explains, for example, why HIV virus particles can infect only mammalian cells which display a very specific protein (called the CD4 receptor protein) on the cell surfaces.

This requirement for complementary binding configurations (between a virus surface protein, and a cell surface protein) helps explain how and why free $Zn^{++}$ ions (which are released when a zinc salt is dissolved in saliva, a lubricant gel, or some other aqueous liquid) block virus infections. When the positively-charged zinc ions settle into negatively charged protein sites on viral surface proteins or cell surface proteins, the $Zn^{++}$ ions alter the binding characteristics of the surface proteins, thereby altering and temporarily destroying the normal electrical configurations and binding affinities of those proteins. This is analogous to jamming a toothpick or other foreign object into a keyhole;

so long as the foreign object remains jammed in the keyhole, the key that normally operates that lock is not able to fit into the keyhole.

This "protein-jamming" mechanism has been recently described, in the context of cold-causing rhinoviruses, in Novick et al 1996.

A second mechanism also contributes to the anti-viral activity of zinc salts. When a zinc-containing lubricant is used during intercourse, as described herein, the binding of $Zn^{++}$ ions (released by the zinc salt in the lubricant) to negative local charges on viral surface proteins causes virus particles to agglomerate and bind randomly to each other, and to the surfaces of cells that cannot be infected, including epidermal and epithelial cells on the skin and mucous membrane surfaces of the penis and vagina. These random binding reactions reduce the ability of the bound viruses to contact and infect cells that are susceptible to active infection by the viruses. For example, by the time an epidermal or epithelial cell reaches a skin or mucous membrane surface, it typically becomes relatively inactive metabolically, and cannot support active replication of viruses inside the cell. This is one of the mechanisms that skin uses to protect the body against viral infection, and it explains why a person who suffers from a disease which causes genital lesions, such as herpes or syphilis, suffers from at least a 100-fold increase in the risk of infection by a virus such as HIV. Accordingly, since normal and healthy epidermal or epithelial cells on a genital surface cannot support active viral replication, the random crosslinking of virus particles to the surfaces of cells (effectively "gluing" the viruses to cells that are already dead or dying) is a very effective mechanism for preventing the glued-on viruses from contacting and infecting other cells that would be susceptible to an active infection.

These protein-jamming reactions and random crosslinking reactions, both of which are caused by free $Zn^{++}$ ions that have been released by zinc salts dissolved in aqueous liquids, apparently were never reported in any scientific or medical reports prior to 1996. Before 1996, the prior art reported a number of postulated mechanisms that apparently had contributed to the antiviral activity of zinc salts in various assays, including: (i) interference with post-translational processing of capsid polypeptides in rhinoviruses (Korant and Butterworth 1976); (ii) inhibition of DNA polymerase in herpes viruses (Shlomai et al 1975; Fridlender et al 1978); (iii) interference with herpes protein synthesis (Gupta and Rapp 1976); (iv) inhibition of thymidine kinase accumulation and a possible alteration of RNA synthesis in vaccinia viruses (Zaslavsky 1979); and (v) interference with procapsid synthesis in foot-and-mouth disease viruses (Firpo and Palma 1979). All of these reported mechanisms apparently are consistent with the ability of free zinc ions to form crosslinking bonds with proteins. Therefore, the protein-jamming and protein-crosslinking mechanisms described above help offer a unifying explanation for the various other molecular mechanisms that also have been postulated in the prior art.

Various zinc salts that were tested in in vitro tests (described in the Examples) against herpes viruses and HIV were shown to be highly effective in inhibiting those viruses. It is believed that, because of the various molecular mechanisms discussed above, zinc can also inhibit, to at least some level, other types of sexually transmitted mammalian viruses, such as hepatitis viruses and papilloma viruses. However, it is much more difficult, time-consuming, and expensive to test agents for their ability to inhibit hepatitis, papilloma, and HIV viruses, than to test such agents against herpes viruses, which are simple and easy to culture in a lab, and which infect numerous types of transformed (immortalized) cell lines that can be grown easily in a lab. Herpes viruses are comparable to weeds; they'll grow quickly, in nearly any type of soil. By contrast, HIV, hepatitis, and papilloma viruses are comparable to highly specialized plants that need special combinations of soil, water, and sunlight before they'll grow well.

Accordingly, herpes simplex viruses are used and regarded herein as a "benchmark" type of standard for anti-viral testing. Herpes simplex viruses can be used in quick, simple, inexpensive assays to evaluate the potency of any candidate zinc compound, at any concentration of interest, and in any aqueous carrier fluid or other formulation of interest.

It is believed that, since herpes simplex viruses tend to be more hardy, opportunistic, and non-specialized than HIV, hepatitis, or papilloma viruses, and since anti-viral zinc works by means of a "protein jamming" activity that inhibits the essential step of viruses binding to susceptible cells, a zinc salt which potently inhibits herpes simplex viruses (and HIV, as shown in the Examples) also can inhibit hepatitis and papilloma viruses as well. However, it should be recognized that the anti-viral utility of zinc in a genital lubricant is fully supported by zinc's ability to block even a single type of sexually transmitted virus, such as herpes viruses and/or HIV, regardless of whether it can also block other types of viruses, such as hepatitis or papilloma viruses.

Finally, it also should be noted that zinc has no reducing or oxidizing potential. Unlike iron, copper, manganese, and the other transition metals, zinc does not try to alter the electron status of proteins or DNA, either by trying to shed unwanted electrons (like hydrogen and other "reducing" agents), or by trying to take away electrons (like oxygen and other "oxidizing" agents). This makes zinc well-suited for stable, non-damaging interactions with proteins and other biomolecules.

SUITABLE ZINC SALTS

One of the most important initial discoveries, in the series of steps that led to the subject invention, was the discovery by the Applicant that certain types of water-soluble zinc salts do not cause any noticeable irritation, to either males or females, when used in lubricant gel formulations during a complete act of intercourse, even when these zinc salts were included at surprisingly high concentrations (i.e., in levels that were measured as percentages, by weight, rather than just millimolar or comparable terms).

This discovery was significant, and unexpected, for several reasons. First, much of the prior research which used zinc salts against herpes viruses used zinc sulfate, in formulations which cause substantial burning and irritation in most people, especially on mucous membranes. Substantial burning and irritation may be tolerable, when treating outbreaks of herpes lesions in someone who is already infected, since the irritation of the lesions is already present, and the treatment makes the lesions heal and disappear more rapidly. However, that same level of burning and irritation is not as tolerable in a lubricant intended for use during intercourse.

This is not to say that some level of irritation is never tolerated or acceptable, in genital lubricants used during intercourse. For example, it is well-known that spermicidal surfactants (such as nonoxynol or octoxynol) cause irritation in many users; however, such irritation is generally regarded as tolerable, by users who want and desire that type of contraceptive activity. Nevertheless, the irritation caused by topical zinc sulfate mixtures, when used for treating outbreaks of herpes lesions in already-infected people, taught away from the use of zinc salts in lubricants for use during intercourse.

Second, the discovery that various zinc salts (such as zinc acetate and zinc propionate) did not cause any irritation, when dissolved in a gel, was also surprising, since zinc acetate and zinc propionate each caused a substantial amount of burning and irritation to the skin, when dissolved in water alone. This unexpected disappearance of irritation when zinc acetate or propionate were dissolved in a complete gel formulation rather than water, is described in more detail below.

And third, zinc salts are well known to be astringents (agents that cause a drying effect, blood vessel constriction, and/or tissue contraction). The Merck Index (11th edition, 1989) explicitly indicates that the majority of the zinc salts that are of pharmaceutical interest are astringents. Astringents are well-suited for treating outbreaks of herpes lesions, since one of the main goals of treating herpes lesions is to dry out the virus-laden fluid that fills the blisters and lesions. However, an astringent is the opposite of what people normally want in a lubricant, especially a lubricant applied to the genitals during intercourse. People do not want drying, vasoconstricting, or other astringent actions at their genitals during intercourse. Therefore, the fact that zinc salts are astringents teaches away from their use in genital lubricants.

However, in this invention, the use by the Applicant of a suitable carrier fluid containing water, as well as thickening and lubricating agents, overcame the astringent effects of zinc. No unpleasant or noticeably astringent effects were observed by the volunteers who tested gels containing any zinc salt during intercourse.

As mentioned above, the anti-viral activity of a zinc salt in a suitable carrier fluid is due to the action of free divalent zinc ions that have been released by the salt. Three of the most important factors in determining the concentration of zinc ions that are present in an aqueous fluid when a certain zinc salt is dissolved in that fluid are:

(1) The solubility of the zinc salt in water. This value is often expressed in terms of grams of salt per 100 cubic centimeters (0.1 liter) of saturated solution. That figure can be converted into a grams/liter basis by multiplying it by 10.

(2) The molecular weight of the salt, which allows a weight concentration to be converted into a molar concentration. For example, the molecular weight of zinc acetate (in anhydrous form, without any associated water molecules) is 183.4, so 183.4 grams of zinc acetate is equal to one mole (=$6.02 \times 10^{23}$ molecules). Preparations that have associated water, such as the dihydrate form, have higher molecular weights, to account for the water; the dihydrate salt weighs 219.4 grams/mole of zinc acetate. Molar concentrations are usually expressed in molar (M) units, which refer to moles of a compound per liter of solution, or in millimolar (mM) concentrations, which refer to thousandths of a mole per liter.

(3) The rate at which the salt dissociates into cations and anions. This is usually expressed on a base 10 logarithmic scale using pK values, which are often called equilibrium constants, stability constants, or dissociation constants. Like pH values for acids, if the pK value of a salt is low, the ionic dissociation of that salt is high.

Solubility and pK values for several zinc salts are provided in Table 1. These values were obtained from published reports (Sillen and Martell 1964 and 1971, Lide 1990, Linke 1965, and Cannan and Kibrick 1938). There are several methods for measuring ion concentrations, and variations in values between different published papers reflect differences in the method of measurement. In addition, based on a review of several articles cited by Sillen and Martell, it appears that reported pK values of less than 2 refer to the release of a single carboxy anion from a zinc salt, while reported pK values of more than 2 (e.g., Griessar et al 1968) refer to the release of free divalent zinc ions, which occurs when both of the carboxy anions dissociate from the zinc.

All of the organic zinc salts listed in Table 1 are good candidates for use in anti-viral lubricants as described herein. Two salts which were specifically tested for irritation during intercourse, because they have high solubility in water and high ionic dissociation rates (low pK values), are zinc acetate and zinc propionate. Neither of these salts caused any irritation to either the male or female, even when added to K-Y Lubricating Jelly (as a carrier fluid) at a concentration of about 5% w/v. It should be noted, however, that both zinc acetate and zinc propionate caused vaginal irritation, when dissolved in water alone.

Another preferred salt which merits specific attention is zinc lactate, since it releases lactate ions, which are naturally present at high concentrations inside any healthy vagina, since the vagina secretes relatively high quantities of lactic acid to help suppress microbial infections. Therefore, the epithelial and epidermal membranes of the genitals are well-adapted to cope with large quantities of

TABLE 1

SOLUBILITY AND IONIC DISSOCIATION (IN WATER) OF VARIOUS ORGANIC SALTS OF ZINC

| Salt | Solubility (grams/liter) | Molecular weight | Molar solubility (moles/liter) | Reported pK values |
|---|---|---|---|---|
| Zinc acetate | 300 (25° C.) | 183.4 | 1.64 | 1.03 |
| Zinc propionate | 320 (15° C.) | 211.5 | 1.51 | 1.01 |
| Zinc butyrate | 107 | 275.6 | 0.4 | 1.00 |
| Zinc formate | 52 (20° C.) | 155.4 | 0.33 | $pK_1 = 0.6$, $pK_2 = 0.95$ |
| Zinc gluconate | 127 (25° C.) | 455.7 | 0.28 | 1.70 |
| Zinc glycerate (dihydroxypropionate) | NA | 275.6 | NA | 1.80 |
| Zinc glycolate (hydroxyacetate) | NA | 215.5 | NA | 1.92 |
| Zinc lactate | 57 | 279.5 | 0.20 | 1.86 |

TABLE 1-continued

SOLUBILITY AND IONIC DISSOCIATION (IN WATER)
OF VARIOUS ORGANIC SALTS OF ZINC

| Salt | Solubility (grams/liter) | Molecular weight | Molar solubility (moles/liter) | Reported pK values |
|---|---|---|---|---|

Sources:
Cannan and Kibrick, J. Amer. Chem. Soc. 60: 2314 (1938)
Sillen and Martell, Stability Constants of Metal Ion Complexes, Spec. Publ. 17 & 25 (The Chemical Society, London, 1964 and 1971)
CRC Handbook of Chemistry and Physics, 71st Edition (Boca Raton, FL, 1990)
Linke, W.F., ed., Solubility of Inorganic and Metal Organic Compounds, 4th Edition, 1965 lactate ions. When added to K-Y Lubricating Jelly (as a carrier fluid) at a concentration of about 5% w/v, as used as a lubricant during intercourse, zinc lactate caused no irritation of any sort to either the male or female.

Zinc pyruvate also deserves special attention, since it releases pyruvate ions, which are a substrate that cells use to generate energy during the process of glycolysis. Pyruvate is the intermediate that feeds the so-called "Krebs cycle", in which the metabolites formed from glucose are broken down to carbon dioxide and water, to release large quantities of energy. By providing an active agent that can boost cellular metabolism, zinc pyruvate in a topical genital lubricant may be useful in treating various urinary, gynecological, dermatological, or sexual disorders, such as impotence and post-menopausal discomfort.

Various other water-soluble salts of zinc are also known to those skilled in the art. For example, other organic zinc salts that are not widely used but which have relatively low molecular weights include zinc gallate and zinc glycerate.

Another class of organic salts that can be used if desired include salts that can be made from di-carboxylic acids (which have two carboxy groups on a single molecule), such as maleic acid, malonic acid, and succinic acid. The corresponding zinc salts are zinc maleate, zinc malonate, and zinc succinate.

Zinc gluconate was also tested, using in vitro tests against herpes viruses, as well as genital irritation tests using human volunteers. It did not cause any irritation during intercourse, and as described in the Examples, it is clearly effective in preventing infection by herpes viruses, in in vitro tests.

There are two different commercially available forms of zinc gluconate: a granular preparation, which has substantial grittiness and which is comparable to salt or sugar but with uneven particle sizes; and a powdered form, which is much finer and does not have any coarseness or grit. Both forms are available from companies such as Generichem (Totowa, N.J.) or Amend Drug & Chemical Company (Irvington, N.J.). Apparently, the granular form is generally preferred for manufacturing use, since it does not generate as much airborne dust as the powdered form.

The preparation that was purchased and tested in the late 1980's was the granular form, which does not have a high degree of solubility in water. Even after it was mixed with water and extensively and carefully grinded by hand, using a mortar and pestle, followed by thorough mixing in a gel, the gel contained a visible suspension of very fine, small particles which displayed a very slight roughness when rubbed hard between the forefinger and thumb. Although no abrasion or irritation was noticeable by either volunteer when this gel was tested for irritation during intercourse, it was not deemed to be preferred for use in a genital lubricant, due to the risk of creating microabrasions that might help viral particles penetrate skin or mucous membranes.

However, in 1997, a supply of powdered (rather than granular) zinc gluconate was purchased from Amend Drug & Chemical Company (Irvington, N.J.). The powdered form was substantially more soluble in water, and did not leave any detectable grit or fine particles after being mixed with water and/or a gel. Accordingly, it is a preferred candidate for use as described herein.

Other organic salt candidates that are less soluble in aqueous solution and/or have relatively high pK values include zinc salicylate, zinc citrate, zinc oleate, zinc benzoate, zinc laurate, and zinc tartrate. Several other organic salts of zinc were obtained and evaluated, including zinc stearate, zinc salicylate, and zinc valerate. None of those salts caused any irritation during forearm or male genital tests.

Although non-polymeric salts with low molecular weights are preferred, this invention includes zinc salts formed from a polymeric component of a gel, such as a cellulose derivative or some other polymer or polysaccharide used as a thickening or lubricating agent. Several such polymeric thickening or lubricating agents, which can be converted into polymeric zinc salts for use herein if desired, are described below.

INORGANIC SALTS; ZINC CHLORIDE AND SULFATE

In the series of patents issued to Kelly, cited above (including U.S. Pat. Nos. 5,208,031; 5,482,053; 5,545,673; and 5,599,551), water-soluble organic salts of zinc that have low molecular weights, as discussed above, are preferred for use in anti-viral genital lubricants as disclosed herein, since those organic salts did not cause any noticeable irritation when used as additives in genital lubricants that were tested for irritation, during intercourse. By contrast, in the initial tests described in those patents, the two inorganic salts (zinc chloride, and zinc sulfate) that were tested caused significant irritation.

However, the use of inorganic salts such as zinc chloride and zinc sulfate is feasible. Preferably, in lubricants that use such salts, steps should be taken to reduce or minimize the irritation they can cause in the absence of such steps. If inorganic salts are being considered for such use, certain factors should be kept in mind, including the following.

First, zinc chloride and zinc sulfate ionize at very high rates (at levels approaching 100%, releasing essentially all of their zinc in the form of free divalent ions) when dissolved in an aqueous solution. By contrast, even the most highly ionizing organic salts (such as zinc acetate) tend to ionize at rates of about 30% or less (as indicated by pK values of about 1, or higher). Accordingly, smaller quantities of zinc chloride or zinc sulfate (or various other inorganic salts) are required to provide a given concentration of zinc ions, compared to the quantities of organic salts required to provide the same level of ions. This simple factor (i.e., a reduction in the quantity of the salt) can reduce or avoid irritation caused by a highly ionizing inorganic salt such as zinc chloride or sulfate.

Second, highly-ionizing zinc salts, when dissolved in an aqueous solution, will make the solution acidic. When positively charged zinc ions are dumped into solution by a highly-ionizing salt, the $Zn^{++}$ ions bind with negatively-charged hydroxyl ($OH^-$) ions, which are released when water molecules spontaneously dissociate into $H^+$ and $OH^-$ ions. This binding, between $Zn^{++}$ ions and $OH^-$ ions, reduces the number of free $OH^-$ ions. This in turn increases the number of "stranded" hydrogen protons ($H^+$) in the solution, since those ions no longer have a balanced number of $OH^-$ ions with which they can interact. This increase in $H^+$ ions is, quite simply, an increase in acidity, since acidity in an aqueous solution is a direct measurement of $H^+$ ion concentration. It is not the $Zn^{++}$ ions in solution which irritate the skin; instead, it is the increase in acidity caused by binding of the zinc ions to $OH^-$ ions. Accordingly, highly ionizing salts such as zinc chloride or sulfate, which release more $Zn^{++}$ ions cause greater acidity, compared to organic zinc salts.

As a demonstration, when 5% (weight per volume) solutions were prepared from zinc acetate and zinc lactate in distilled deionized water, the pH of each solution was about 6.2. By comparison, when a 5% solution of zinc sulfate was prepared, its pH was about 5.6. Since the pH scale is logarithmic, and a drop of 1 pH unit indicates 10-fold greater acidity, a pH drop of 0.6 (from 6.2 to 5.6) indicated about 4 times as much acidity in the zinc sulfate solution as in the zinc acetate or lactate solutions.

In a genital lubricant, this increased acidity can be eliminated or minimized by adding a neutralizing or buffering agent to the lubricant formulation. A neutralizing agent is an alkaline compound (such as NaOH, sodium hydroxide) that releases $OH^-$ ions (along with a stable cation, such as $Na^+$) in sufficient quantities to neutralize or at least reduce the increase in acidity caused by an acidifying agent such as zinc chloride or sulfate.

A buffering compound (such as $NaHCO_3$, sodium bicarbonate) partially dissociates at a neutral pH (pH 7), in a manner that allows its equilibrium dissociation levels to be pushed in either direction, by either an acid or alkali. If an acid is added to a solution containing a buffer, the buffer will be pushed in a direction that minimizes the effects of the acid, to help keep the pH of the solution relatively stable and close to neutral. Conversely, if an alkali is added to a solution containing a buffer, the buffer will shift in the opposite direction, thereby minimizing the effects of the alkaline compound and helping keep the pH of the solution relatively close to neutral.

Various neutralizing and buffering agents known to those skilled in the art are physiologically acceptable and otherwise suitable for a topical genital lubricant formulation. As one example, K-Y Lubricating Jelly contains a strong alkali, sodium hydroxide (NaOH), as a neutralizing agent to reduce the acidity of other components of K-Y Jelly. By itself, sodium hydroxide is lye, which is extremely irritating to the skin. However, if added to an acidic mixture, a proper quantity of sodium hydroxide simply neutralizes the acid and prevents the acid from causing irritation.

Accordingly, highly-ionizing salts (including inorganic salts such as zinc chloride or sulfate, as well as organic salts such as zinc acetate or propionate) can be used in genital lubricants. If the concentration of a highly-ionizing zinc salt in a lubricant causes undesired acidity, the acidity can be reduced by any or all of several techniques, including: (i) limiting the quantity of the highly-ionizing salt; (ii) using two or more salts in combination; and (iii) adding a neutralizing or buffering agent.

In addition to the various salts listed above, other zinc compounds (including various zinc "complexes") are also suitable for use as disclosed herein. These include various zinc complexes listed and shown in articles such as Merluzzi et al 1989, which tested a large number of zinc salts and complexes in order to rank their anti-viral activities in cell culture tests. In general, "complexes" is a vague and imprecise term when used in the context of molecules that contain metal atoms; it generally refers to molecular compounds that contain one or more metal atoms, but which do not release the metal ions into solution as readily as other compounds which are deemed to be "salts". Although arbitrary classifications that depend on numerical pK levels are used by some researchers to create arbitrary boundary lines between zinc salts and zinc complexes, there is no natural dividing line between a zinc salt and a zinc complex. Accordingly, any zinc complex or other zinc compound which is soluble in water, and which releases free zinc ions ($Zn^{++}$) in quantities that are effective in inhibiting at least one type of sexually transmitted virus (in in vitro tests), when dissolved in an aqueous solution, is regarded herein as a zinc salt.

If a non-salt zinc compound (such as zinc oxide, as one example) is added to a topical formulation as disclosed herein, along with a solubilizing agent that weakens or otherwise alters the chemical bond(s) between the zinc and the covalently bound atom(s) in the compound, thereby causing release of significant quantities of free zinc ions from the zinc compound in the presence of the solubilizing agent, the net result is functionally equivalent to providing a zinc salt as a single initial ingredient. Accordingly, if a mixture of such reagents (i.e., a non-salt zinc compound, plus a solubilizing agent) is added to a topical genital formulation as disclosed herein, such a combination is regarded as the addition of a zinc salt to the formulation.

ZINC CONCENTRATION RANGES

Rather than trying to determine a single concentration of a zinc salt that would be optimal for everyone, the effectiveness of this invention can be enhanced by designing, manufacturing and selling lubricants having a range of different zinc concentrations, for different people. By way of analogy, since some people are easily sunburned while others are highly tolerant of direct sunlight, suntan oils and creams are sold with a range of "sun protection factors." Anyone is free to choose his or her preferred formulation, based on skin type, anticipated exposure levels, and other factors. As another example, contraceptive gels ranging from 1% to 4% nonoxynol, and condoms lubricated with fluids ranging from 5% to 15% nonoxynol, are sold over-the-counter, and purchasers are free to choose the concentration they prefer.

In a comparable manner, genital lubricants having a range of concentrations of anti-viral zinc salts can be made available, and people can choose the concentrations they prefer, depending on various factors such as personal preferences and the type of lubricant they're using. People who are at relatively low risk, or who have sensitive skin or are highly susceptible to psychosomatic suggestions of irritation, might prefer to use a formulation having a relatively low concentration, such as about 0.5% to 5%, expressed as weight per volume (w/v, calculated as grams of zinc salt per milliliter of fluid, multiplied by 100 to convert the ratio to a percentage). People who are at higher risk might choose to use a lubricant containing 30% or more of a zinc salt. With respect to this 30% figure, it should be noted that:

(1) It indicates the weight of the salt, rather than the weight of elemental zinc. For example, a compound containing 30% w/v zinc acetate would contain about 10.7% elemental zinc.

(2) Preparations used for other surface applications are sold over-the-counter which contain more than 30% elemental zinc.

(3) Relatively small quantities of lubricant are typically used in conjunction with condoms. For example, while spermicidal gels for use without condoms usually contain about 5% or less nonoxynol, many condom lubricants contain up to 15% nonoxynol. Accordingly, a pre-packaged condom lubricant may have a somewhat higher concentration of a zinc salt than a stand-alone gel intended for use without a condom.

(4) The lubricant usually becomes diluted by the female's natural fluids after intercourse begins.

Accordingly, preferred zinc concentrations in genital lubricants disclosed herein that contain organic zinc salts are in the range of about 0.5% to about 30% w/v, whereas preferred zinc concentrations in genital lubricants containing highly ionizing zinc salts (such as zinc chloride or zinc sulfate) are lower, such as in a range of about 0.03% to about 5%.

In general, the anti-viral efficacy of a zinc-containing lubricant will increase as the concentration of zinc (and free zinc ions) increases. However, the propensity of a lubricant to cause irritation will increase, as higher quantities of zinc are used, and when highly-ionizing salts are used. Accordingly, preferred zinc concentrations will seek to achieve high levels of anti-viral efficacy with low levels of irritation. As noted above, preferences regarding concentration will vary among different users. By way of illustration, some people prefer ultra-thin condoms, because they believe such condoms interfere less with sensitivity and pleasure, while other condom users regard ultra-thin condoms as having too great a risk of breakage. In a similar manner, some users will prefer lubricants with very low levels of zinc, in order to minimize any risk or even any mental suggestion of irritation, while other users will prefer lubricants that have higher concentrations of zinc, even though such lubricants may cause some irritation.

It also should be kept in mind that the invention herein discloses genital lubricants that caused no detectable irritation, in the human volunteers who tested them. Instead of being a toxin or a surfactant that aggressively attacks and kills cells, zinc is actually a soothing and protective topical agent, as demonstrated by its presence as the main active ingredient in various skin-soothing and skin-protective formulations, such as calamine lotion, and ointments that help soothe and cure diaper rash in infants.

BI-FUNCTIONAL LUBRICANTS WITH ADDITIONAL ACTIVE AGENT(S)

A zinc salt as disclosed herein may be added as an anti-viral additive to a genital lubricant that also contains one or more additional active agents that are intended to achieve other functions. For example, a zinc salt can be added to a lubricant that also contains nonoxynol, a widely-used spermicidal surfactant. The resulting lubricant could be regarded as a "bi-functional" lubricant, since it would have two active agents that provide two different desired functions, in a relatively inert carrier liquid; the nonoxynol would provide a spermicidal contraceptive agent, and the zinc salt would provide an anti-viral agent. The nonoxynol is likely to cause some level of irritation, in at least some users; this is a regrettable but well-known side effect of spermicidal surfactants such as nonoxynol and octoxynol, which attack and destroy the lipid bilayer membranes that surround sperm cells and other mammalian cells.

Irritation tests on human volunteers indicate that zinc can actually reduce the physical irritation that is caused by nonoxynol, in users who are sensitive to that type of irritation. However, even a reduction in irritation by zinc does not mean that the irritation caused by a second active agent, such as nonoxynol, will be completely eliminated, in the resulting formulation. Accordingly, it should be recognized that "bi-functional" lubricants, containing both an anti-viral zinc compound as one active agent, and a second active agent such as a spermicide or a microbicide, may cause some irritation in some users. Such lubricants are within the scope of the invention disclosed herein, and are covered by the claims below.

"STAND-ALONE" LUBRICANT FORMULATIONS

For "stand-alone" lubricants (i.e., lubricants that are not pre-packaged with condoms), gels and similar aqueous formulations are generally preferred, for various reasons (both scientific and economic) known to those skilled in the art. While the carrier substance used in a particular lubricant is not critical to this invention, in a preferred embodiment the carrier fluid of a lubricant gel as disclosed herein has the following components, which are discussed in more detail in the above-cited U.S. Pat. No. 5,208,031:

a. water;

b. a thickening agent, such as cellulose or a chemically treated derivative of cellulose, acacia, agar, alginate, carrageenan, gum tragacanth, xanthan gum, collagen, carboxypolymethylene, glyceryl monostearate, polyvinylpyrrolidone, and polyacrylamide; and, c. a lubricating agent, such as glycerin, propylene glycol, polyethylene glycol, polypropylene glycol, polyisobutene, polyoxyethylene, behenic acid, behenyl alcohol, sorbitol, and polydimethylsiloxane.

The thickening and lubricating agents listed above are relatively inactive biologically, and basically serve as carrier substances.

As used herein, "lubricating agent" refers to a component which is incorporated into a genital lubricant for the purpose of reducing friction during intercourse. Although any liquid (including water) sometimes functions as a "lubricant" in the broadest sense of the word, four characteristics distinguish a preferred lubricating agent, for purposes hereof, from water and other liquids that do not have the characteristics preferred for effective and comfortable lubrication during sexual intercourse. A preferred lubricating agent: (1) is substantially more viscous than water and feels slippery when rubbed between two skin surfaces; (2) has an affinity for human skin, and when applied to skin, it spreads smoothly and evenly across the contacted area; (3) remains in contact with the skin, clinging to it in a more substantial manner than water, which is easily wiped away; and, (4) has a low level of volatility, and does not evaporate quickly or become sticky.

The foregoing characteristics can be easily recognized and understood, on a practical level, by rubbing a conventional lubricating agent (such as glycerin or mineral oil) between the fingers. The nature and the durability of the lubrication, and the differences between such agents and other liquids such as plain water, are readily apparent.

In addition, in order to be physiologically acceptable (in contrast to lubricants such as motor oil, which are not physiologically acceptable), preferred lubricating agents are gradually broken down into innocuous substances in the body (in cases in which they are absorbed by tissue to a significant degree through the skin or mucous membranes), or they are of a nature that allows them to be secreted by the vagina and washed cleanly from the skin. In either case, they do not foul or clog the pores in skin or mucous membranes, leave any unacceptable residues, or cause other adverse effects if used repeatedly over a span of months, during numerous acts of intercourse.

Several lubricating agents which are used in commercially available sexual lubricants satisfy these criteria, including glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and certain naturally-occurring compounds (such as behenic acid, derived from various types of seeds and animal fats) and their derivatives (such as behenyl alcohol) are also used as lubricants in cosmetics and other formulations that contact the skin. In addition, some sugar-alcohols such as sorbitol, and some silicon compounds such as polydimethylsiloxane, are also used as skin-contacting lubricating agents.

Because glycerin, propylene glycol, polyethylene glycol, and polypropylene glycol have long been used in genital lubricants and other skin-contacting formulations with no adverse effects, and since these compounds can be synthesized easily and inexpensively without requiring extensive purification from natural sources, they are preferred for use as lubricating agents in the anti-viral sexual lubricants of this invention. The suitability of any other candidate lubricating agent in a zinc-containing genital lubricant formulation as described herein can be determined through routine experimentation in humans and in in vitro cell culture and in vivo lab animal tests to determine its efficacy and appropriateness. In view of the variety of known lubricating and thickening agents that are physiologically acceptable for topical use, the selection of a preferred lubricating or thickening agent will depend on economic factors as well as scientific and medical factors.

Derivatives of cellulose which have been chemically treated to make them more hydrophilic (such as hydroxyethyl and hydroxymethyl derivatives, which have numerous additional hydroxy groups bonded to the starting cellulose molecules) have been widely used as thickening agents in gels that are applied to the skin. Other thickening agents that have been used in skin-contacting compounds, and which offer candidate agents for use in zinc-containing genital lubricants, include acacia, agar, alginate, carrageenan, gum tragacanth, xanthan gum, collagen, carboxypolymethylene, glyceryl monostearate, polyvinylpyrrolidone, and polyacrylamide.

Other components, including preservatives (such as chlorhexidine gluconate), anti-crystallization agents (such as glucono-delta-lactate), fragrances, coloring agents, alkaline or acidic or buffering agents to maintain the proper pH, and soothing or anti-swelling agents (such as lanolin, aloe vera extract, or hydrocortisone) can be added to the genital lubricants described herein.

In order to overcome the normal astringent effects of most zinc salts, preferred carrier substances are liquids (such as a gel) or other fluids (such as a cream, ointment, or emulsion). If desired, it is also possible to incorporate zinc salts into carrier formulations, such as microencapsulated or dry formulations, that do not fit clearly into a category of liquid or fluid. If a powdered-type lubricant is being used, a zinc compound that does not have astringent effects is preferred.

In a preferred embodiment, the complete lubricant mixture is physiologically safe and acceptable when used repeatedly, during numerous acts of intercourse, over a period of months or years.

PACKAGING FOR STAND-ALONE LUBRICANTS

Packaging for the articles of manufacture disclosed herein is not critical to this invention. By way of illustration, a variety of different packages are used for (i) condoms, which are usually packaged in sealed plastic or foil packages with a single condom in each sealed sterile package; (ii) "stand-alone" lubricants; and (iii) viscous gels intended for insertion deep into the vagina, using an applicator.

In a preferred embodiment, a "stand-alone" lubricant is packaged, shipped, and handled in a package that renders it convenient and useful as a lubricant during intercourse. Types of packaging that are commonly used for stand-alone gels and similar formulations include:

(1) A watertight tube made of deformable metallic foil. Such tubes usually are sealed at one end by means such as crimping, and have an outlet orifice at an opposed second end, which can be covered and sealed by a removable and/or openable device such as a threaded or flip-top cap. Such metallic foil tubes are commonly used to hold toothpaste, ointments, and gels such as K-Y Lubricating Jelly and contraceptive gels. When squeezed to dispense a quantity of lubricant, a deformable metallic tube does not seek to regain its original shape after the squeezing pressure is released. By avoiding the creation of a vacuum inside the tube which would draw air into the tube, this minimizes oxidative discoloration or degradation of the lubricant in the tube. In addition, another advantage of a metallic container in this particular context is that it can be placed in a cup or glass of warm or hot water, such as on a table or nightstand next to a bed. The metallic walls of the tube quickly convey heat from the warm water into the lubricant; this warms the lubricant to a pleasant temperature before it is applied to the genitals. This procedure encourages consistent rather than sporadic use, and can help make the step of applying the warm lubricant a pleasant form of foreplay, rather than a distracting annoyance of a cold fluid to the genitals. Anything which enhances a sense of warm pleasantness when applying such a lubricant helps promote consistent use, and substantially increases the level and efficacy of the anti-viral protection provided by the zinc additive in the lubricant.

(2) A watertight tube with deformable plastic walls, permanently sealed at one end (such as by heat-crimping), and have a removable cap covering an outlet orifice at the other end. Such tubes are commonly used to hold toothpaste, ointments, and gels such as K-Y Lubricating Jelly and contraceptive gels. The cap can be a threaded screw-on cap, or a hinged flip-type cap which can be opened without detaching it from the tube, so that it cannot be lost, and can be opened or closed easily with one hand. Between the two ends of the tube, the container has at least one deformable plastic wall, which in a preferred embodiment is essentially tubular, comparable to a toothpaste tube, with a transitional shoulder or neck region leading to the outlet orifice.

Figure 5:
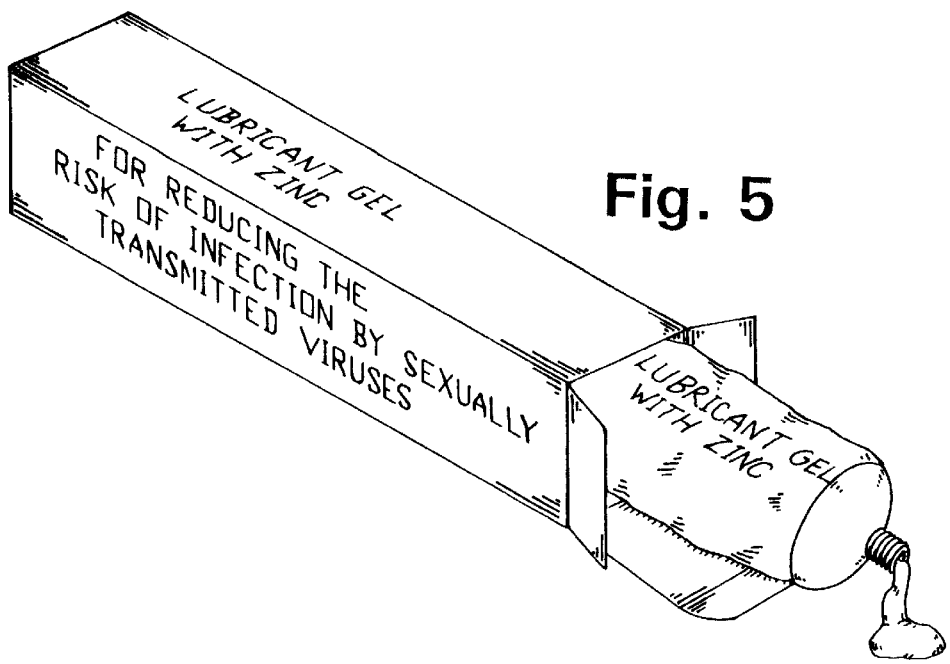
FIG. 5 depicts a tube containing a "stand-alone" lubricant (i.e., a fluidized lubricant formulation such as a gel, that is not pre-packaged with a condom). The lubricant contains an anti-viral zinc salt.

FIG. 5 shows an example of a watertight tube, made of either metallic foil or plastic, containing a gel with an anti-viral zinc salt.

(3) A small, flat, watertight packet which contains a sufficient quantity of lubricant for a single use during intercourse (such as about 5 to 10 milliliters, or about 1 to 2 teaspoons). Such packets can be made of plastic, metallized foil, or other suitable material. This type of small sealed packet allows the lubricant to be conveniently and discretely carried in a purse, pocket, glove compartment of a car, or other location without the bulk or conspicuousness of a full-sized tube.

(4) A small single-dose container made of a breakable plastic or other material, which can be opened by breaking off a component that protrudes outwardly from the container, thereby unsealing an outlet orifice. This type of device is comparable to a miniature version of the plastic bottles with break-off tops that are widely used for non-carbonated children's drinks.

(5) A stiff-walled bottle, normally but not necessarily in an upright configuration, with a wall (typically cylindrical or with an elliptical or similar cross-sectional shape) made of plastic, glass, or other suitable material. When such containers have deformable plastic walls, they are simply another form of watertight tube, which can be squeezed when the cap is open to dispense the fluid contained therein. Alternately, such bottles are often equipped with a dispenser-type device (usually mounted on top, as part of a cap assembly) that allows a quantity of the lubricant to be conveniently dispensed when manually operated, such as by depressing a plunger mechanism. Such plunger-type dispensers are widely used for dispensing creams, ointments, fluidized soaps, or other fluids from such bottles. This allows a desired quantity of the fluid to be placed on the palm or fingers of one hand while the other hand remains dry and clean; alternately, it would allow a genital lubricant to be placed directly onto the surface of the penis, without getting any of the lubricant onto either hand.

(6) A vaginal insertion device, which is designed to insert and emplace a gel, foam, or similar fluid deep enough inside a vagina so that the fluid coats and blocks the entrance to the uterus. Such devices, which are widely used with contraceptive gels and foams, typically comprise a cylindrical barrel which is properly sized for comfortable insertion into a vagina. During use, the barrel encloses a slidable plunger or piston component which is manually forced into the barrel from one end, thereby forcing the fluid out of the barrel through an orifice at the other end of the barrel. These insertion devices are commonly sold in two different forms: (1) a disposable single-use form, with a gel-type fluid already loaded inside the chamber, and with the entire article inside a sealed sterile package, for use prior to a single act of intercourse; or (2) a reusable device which is designed to be filled and used repeatedly, prior to each act of intercourse, from a container which holds a sufficient quantity of gel or foam for multiple applications. Either type of device is well-suited for use with zinc-containing lubricants as described herein.

LUBRICATED CONDOMS

Another preferred embodiment of genital lubricants that contain an anti-viral zinc salt involves condom lubricants.

As used herein, "condom lubricant" refers to a fluidized substance that is spread across one or more surfaces of a condom, and which is contained within a sealed watertight package that contains a condom. In other words, "condom lubricant" refers to lubricants that are pre-packaged with condoms, and does not include "stand-alone" lubricants packaged without condoms, as described above. However, it should be noted that "genital lubricant" is a broader term, which includes condom lubricants as well as stand-alone lubricants.

When a zinc salt is included as an anti-viral additive in a condom lubricant, it provides an additional level of protection, beyond the protection already provided by the condom, to further reduce the risk that a person will become infected by a sexually transmitted virus. This type of additional protection is comparable to the ability of nonoxynol, in a condom lubricant, to provide additional protection against pregnancy, in case a condom breaks, or in case the male loses his erection prior to withdrawal and semen spills or leaks out of the condom.

Figure 6:
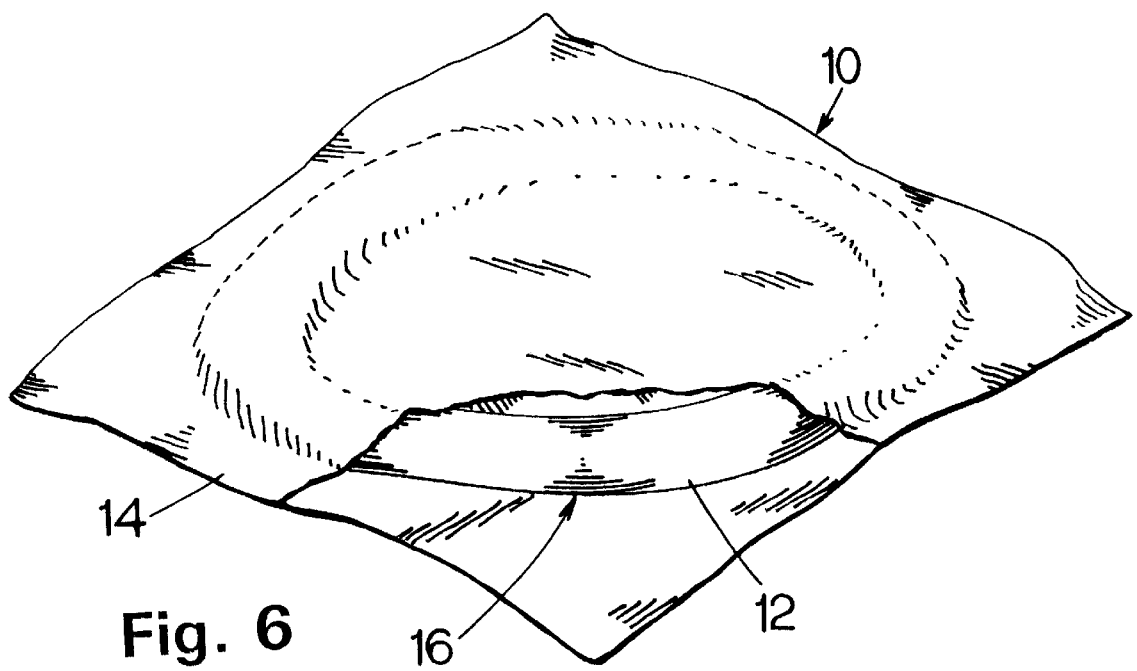
FIG. 6 depicts a condom contained within a sealed package (shown in partial cutaway view) which also encloses a lubricating fluid containing an anti-viral zinc salt.

This article of manufacture 10 is shown in FIG. 6, with a lubricated condom 12 inside a sealed plastic or foil package 14, which also contains a clear lubricating fluid 16.

ABILITY OF ZINC TO INHIBIT HIV

In addition to reducing the risk of infection by herpes viruses, zinc salts used in genital lubricants reduce the risk of infection by the human immunodeficiency virus (HIV). Examples 8–10 below and FIG. 1–4 provide data indicating that in a two-step incubation assay involving a first incubation step, combining zinc acetate with HIV viruses, before susceptible lymphocyte cells are added for a second incubation step, the zinc inhibited or entirely inactivated the HIV particles.

This two-step incubation assay grew out of the realization by the Applicant that, while zinc is toxic to lymphocytes (white blood cells) at the concentrations of interest, such concentrations will never be reached or even approached in the bloodstream, regardless of the concentration of zinc in a topical genital lubricant. As described in Vallee and Falchuk 1993, a review article which discusses the numerous physiological roles of zinc inside the body, the concentrations of zinc in the bloodstream and other bodily fluids are very tightly regulated, since zinc is a crucial cofactor for literally hundreds of enzymes and proteins. If zinc concentration in the blood starts to rise above normal levels, the body responds by using zinc-binding proteins in the blood to bind to the free zinc, thereby sequestering it in inactive form, and by inducing various secretions in the kidneys and pancreas which cause excess zinc to be excreted in the urine and feces.

In view of these factors, it became clear to the Applicant that the standard screening assays used by the National Cancer Institute and others (such as the assays described in Weislow et al 1989) cannot provide an adequate screening test to evaluate anti-viral agents intended for use in topical genital lubricants. The standard assays involve mixing together HIV particles, a candidate anti-viral drug, and susceptible lymphocytes, and culturing all three components together in a single long incubation period. Those assays cannot model or simulate what happens inside a vagina during and after intercourse, where an anti-viral agent inactivates HIV particles before the viruses can penetrate through the skin, enter the bloodstream, and contact susceptible lymphocytes.

Accordingly, to evaluate potential anti-viral agents intended for use in a topical lubricant, the Applicant developed and tested a two-step incubation assay, as mentioned above and as described in more detail in the Examples. The first step of this assay models what happens inside the vaginal cavity. In this part of the assay, the candidate anti-viral agent (such as a zinc salt) was mixed and incubated for a relatively brief period with HIV particles. In the initial studies, carried out using HIV, this initial incubation period was 2 hours. In subsequent tests using herpes viruses (which are much easier to work with than HIV), a range of first-stage incubation times were tested, ranging from 2 hours to only 5 minutes. The duration of the incubation period made no significant difference; as described in the Examples, the anti-viral efficacy of all zinc salts tested was very high, regardless of whether HIV or herpes viruses were used, and regardless of how long the initial incubation period lasted.

Following the first incubation step, the zinc/virus mixture was diluted, by cell culture fluid, to a concentration where: (1) the zinc levels would not be toxic to lymphocytes, but (2) the viral particles would still have sufficiently high concentrations to be highly infective.

Susceptible lymphocyte cells were then added to this mixture, and a second incubation step was carried out for a number of days (20 days or more, when HIV was tested; 3 days, when herpes viruses were tested in plaque assays) to determine whether zinc-treated or untreated viruses would infect the lymphocytes.

The results, shown in FIGS. 1 through 4 for HIV and described in Example 11 for herpes viruses, clearly indicate that the zinc salts were highly effective in suppressing both HIV and herpes simplex viruses.

In addition to these data, the Applicant has discovered that it is valuable that zinc salts in a genital lubricant are toxic to lymphocytes. It has been reported that epithelial cells (which cover the surfaces of mucous membranes) can be infected by HIV, even though epithelial cells do not have the CD4 receptor proteins that HIV particles normally bind to. This infection occurs by means of a cell-cell binding reaction which bypasses the normal virus-cell binding mechanism. In the cell-cell binding reaction, HIV-infected lymphocytes in an ejaculate from an HIV-infected male bind to epithelial cells on the surfaces of mucous membranes. The HIV-infected lymphocytes then inject HIV particles directly into the epithelial cells (Levy 1988; Phillips and Bourinbaiar 1992; Pearce-Pratt and Phillips 1993; Zacharopoulos et al 1992). Therefore, where a genital lubricant contains a zinc salt at a concentration which is toxic to lymphocytes, then the zinc salt reduces or eliminates the ability of HIV-infected lymphocytes in an ejaculate to carry out the cell-cell infection mechanism. This is a highly useful property of zinc-containing genital lubricants which is completely independent of the direct action of zinc ions in inhibiting free-floating virus particles.

It should also be noted that semen and ejaculates contain extraordinarily high concentrations of zinc. While zinc is present in blood at tightly regulated concentrations of only about 1 µg/ml, zinc is present in semen at up to 500 µg/g, and in prostate fluid at up to 1000 µg/g (Eliasson and Lindholmer 1971; Fair et al 1976; Homonnai et al 1978; Marmar et al 1980). In prostate fluid, zinc exerts an antimicrobial effects, to combat infections that cannot be directly combatted by the immune system (Fair et al 1976). And in undiluted semen, zinc suppresses the respiratory activity and motility of sperm cells (Eliasson 1971; Paz et al 1977). Apparently, this allows the sperm cells to stay in a quiescent state, storing and conserving their energy until it is needed. After ejaculation, the zinc is diluted by the female's vaginal fluids and by binding to proteins and cell surfaces inside the vagina. This decrease in the concentration of sperm-bound zinc after ejaculation allows the respiratory activity and motility of the sperm to increase.

The foregoing physiological factors are important, because they indicate that the mucous membranes in the vagina are adapted to withstanding concentrations of zinc hundreds of times higher than lymphocytes can withstand.

EXAMPLES

EXAMPLE 1

IRRITATION TESTS USING ZINC ACETATE

In all examples, the test subjects were a monogamous married couple, free of genital herpes and all other known sexually transmitted viruses.

Zinc acetate was purchased from Pfaltz and Bauer (Waterbury, Conn.). About 0.5 grams were mixed with several drops of distilled water at room temperature. Upon stirring, the salt dissolved completely. The aqueous mixture was rubbed into an area about 3 cm in diameter on the forearm of the male and caused no irritation. Subsequently, about 0.5 grams of the salt were dissolved in a few drops of distilled water, then 10 ml K-Y Lubricating Jelly (sold by Johnson and Johnson, New Brunswick, N.J.) was added to form a gel mixture containing about 5% zinc acetate (w/v). This commercially available mixture contains purified water, hydroxyethyl-cellulose as a thickening agent, glycerin as a lubricant, glucono-delta-lactate to prevent crystallization, chlorhexidine gluconate as a preservative, and sodium hydroxide to reduce the acidity.

The mixture of zinc acetate in K-Y Lubricating Jelly was tested on the male genitals, passively at first and then with active rubbing. It caused no irritation in either test.

When 0.5 grams of zinc acetate was dissolved in distilled water and applied to the shallow region of the vagina by the female volunteer, it caused an unpleasant tingling or mild burning sensation that subsided within about ten seconds. However, when mixed with K-Y Lubricating Jelly (5% w/v as above) and applied to the shallow region of the vagina in a gel mixture, it caused no tingling, burning, or other unpleasant sensation in a passive test.

Subsequently, the gel formulation was applied topically and used as a sexual lubricant during intercourse. Both people wiped off the excess with a tissue after intercourse, but neither person showered or washed off the lubricant until the following day. It caused no irritation to either person.

EXAMPLE 2

IRRITATION TESTS USING ZINC PROPIONATE

Zinc propionate was purchased from Pfaltz and Bauer. About 0.5 grams were dissolved in several drops of distilled water and tested on the male's forearm and genitals. Although no irritation occurred on the skin in either location, the aqueous mixture caused substantial irritation to the urethra.

About 10 ml of K-Y Lubricating Jelly was added to the aqueous mixture, to create a gel mixture of about 5% w/v, which was tested, passively at first and then with active rubbing, on the male's genitals. It did not cause any irritation in either test. Another quantity of a 5% w/v gel mixture was prepared and tested passively in the shallow regions of the female's vagina. It caused no irritation, so it was used as a lubricant during intercourse. Both people wiped off the excess with a tissue after intercourse, but neither person showered or washed off the lubricant until the following day. It caused no irritation to either person.

EXAMPLE 3

IRRITATION TESTS USING ZINC GLUCONATE

In the late 1980's, a granular form of zinc gluconate was purchased from Ruger Chemical Company (Irvington, N.J.). It was gritty and interspersed with hard granules of varying sizes. About 0.5 grams were ground into a fine powder using a mortar and pestle for several minutes. The grinding was repeated after several drops of distilled water were added, and again after 10 ml of K-Y Lubricating Jelly was added. The concentration of the zinc gluconate in the gel mixture was about 5% w/v. This gel was tested on the forearm, male genitals, and female genitals, and subsequently as a lubricant during intercourse. Although it caused no irritation and no abrasion was noticeable by either person during intercourse, the finely ground particles in the gel displayed a very slight roughness when rubbed hard between the forefinger and thumb. Because of the potential for microabrasions caused by the undissolved particles, granular zinc gluconate was not deemed to be preferred for use in a lubricant, unless additional steps were taken to ensure its complete dissolution in the carrier fluid.

Subsequently, it was discovered that some chemical companies sell both a granular form and a powdered form of zinc gluconate. Accordingly, in 1997 a supply of powdered zinc gluconate was purchased from Amend Drug & Chemical Company, which is a subsidiary of Ruger Chemical Company. The powdered form was found to be easily soluble in water at the concentrations tested (up to about 5% w/v), and it did not leave any detectable grit or fine particles after being mixed with water and/or a gel. It was tested for irritation during intercourse, and did not cause any noticeable irritation. EXAMPLE 4

ZINC STEARATE, SALICYLATE, AND VALERATE

Zinc stearate, zinc salicylate, and zinc valerate were purchased from Pfaltz and Bauer. All three salts were tested for irritation on the forearm and male genitals, and none caused any irritation. However, due to other factors such as aroma and solubility, they were not tested during intercourse. EXAMPLE 5

ZINC SULFATE AND CHLORIDE—INITIAL TESTS

Zinc sulfate in crystalline form was purchased from Sigma Chemical Company (St. Louis, Mo.). One gram was ground into a fine powder in a mortar and pestle, then 15 ml of K-Y Lubricating Jelly was added and thoroughly mixed. The mixture did not cause any irritation to the male's forearm, genital skin, or urethra, even when rubbed in actively. However, it caused a tingling, burning sensation when applied in a passive test to the female, so it was not tested during intercourse.

Zinc chloride in crystalline form was purchased from Sigma Chemical Company (St. Louis, Mo.). One gram was ground into a fine powder using a mortar and pestle, then dissolved in water and applied to the forearm of the male. It immediately caused a burning sensation, and was not tested further.

Subsequent work (described below) indicated that the problem of irritation by zinc chloride and zinc sulfate can be overcome, if desired.

EXAMPLE 6

ACIDITY TESTS

After it was recognized that substantial acidity can be generated when highly-ionizing zinc salts are dissolved in water, several zinc salts were tested, to evaluate their effects on pH. All solutions were mixed at 5% w/v concentrations, by weighing out a quantity of the zinc salt into a small bottle, then pipetting a proper quantity of distilled deionized water into the bottle to make up a 5% solution. The zinc lactate did not dissolve immediately, so it was immersed in a water bath at 70° C. and occasionally shaken until the solution became clear. The pH of each solution was then measured. The calibration setting on the pH meter was not working properly, and the meter could not be calibrated to 7.00 using a standard reference fluid; however, the reading remained steady at 7.05 in the neutral calibration fluid, so the readings were deemed to be approximately accurate, and a fixed value of 0.05 was subtracted from each meter reading, to provide the numbers reported below.

The zinc acetate solution (0.8073 g of dihydrate salt, formula weight 219.5, mixed with 13.5 ml water) had a pH of 6.27. The zinc lactate solution (0.2645 g of monohydrate hemi-zinc salt, formula weight 261.6 per mole of zinc, mixed with 4.925 ml water) had a pH of 6.16. The zinc sulfate solution (0.428 g of heptahydrate salt, formula weight 287.5, mixed with 6.755 ml water) had a pH of 5.58, which was substantially more acidic than either the zinc acetate or zinc lactate.

EXAMPLE 7

IRRITATION TESTING OF pH-ADJUSTED ZINC SULFATE

The zinc sulfate 5% solution described above was adjusted to a pH of about 6.8, by adding several drops of 1 N sodium hydroxide solution. A precipitate was formed, but generally resolved upon heating in a 70° C. water bath. This semi-neutralized solution was mixed with an approximately 4× volume of K-Y Lubricating Jelly, to provide a zinc sulfate gel containing about 1% w/v zinc sulfate. It was tested for irritation by human volunteers, and caused no noticeable irritation.

EXAMPLE 8

HIGH-TITER HIV INFECTIVITY TESTS

The initial set of HIV tests were carried out at Biotech Research Laboratories (Rockville, Md.). The HIV-1 viral isolate and H-9 cell line were originally supplied by Robert Gallo of the NCI.

In a first set of tests, 20 mg of zinc acetate powder (ZnAc, MW 183.4) was mixed in 1 ml RPMI cell culture medium (Whittaker Corp.). This 2% (w/v) salt mixture contained 7 mg/ml elemental Zn. Although ZnAc is highly soluble in water, it generated a precipitate in the culture medium, which contains protein. Therefore, a small quantity of HCl was added until the mixture became clear; the pH was about 5.5. The Zn concentration was reduced by half (and the pH was raised somewhat) when an equal volume (1 ml) of cell-free high-titer HIV-1 viral stock was added. The zinc/virus mixture was stirred and incubated for 2 hours at 37° C. (i.e., normal body temperature).

Following this first incubation step, the zinc/virus mixtures were diluted at 1:10, 1:30, and 1:100 ratios using culture medium, and aliquots were added to equal volumes of culture media containing H-9 lymphocytes that had been pretreated overnight with 2 µg/ml Polybreen. The lymphocyte mixtures were incubated for three hours at 37° C.; zinc concentrations during this step were 180, 60, and 18 µg/ml for the 1:10, 1:30, and 1:100 dilutions.

The cell aliquots were then washed twice, using culture medium, to remove free p24 proteins that are present in the initial viral stock. Such proteins will skew ELISA readings if not removed by washing. Cells were then resuspended in fresh medium containing 10% fetal calf serum (FCS) and cultured for 20 days. During this period, each tube was periodically sampled by hand-mixing the tube, withdrawing 100 µl of liquid from the top, and testing the sample for p24 antigens using ELISA assays.

The 1:10 dilutions, which contained 180 µg/ml Zn during the 3-hour incubation prior to washing, caused substantial mortality to the lymphocytes, and resulting ELISA data were discarded.

Based on visual observations, 1:30 dilutions (60 µg/ml Zn) retarded cell growth during the first few days; however, any such effect disappeared within a few days and the cells grew well during the rest of the assay period.

A positive control was used at each dilution. Viral aliquots not treated with zinc were identically diluted, mixed with lymphocytes, cultured, and tested. Negative controls were also run, in which H-9 cells were plated and grown in the absence of any virus or zinc; these provided background levels that vary slightly from day to day, depending on factors such as spectrophotometer calibrations and rinsing conditions.

Optical density (OD) data from the 1:30 dilution test are shown in FIG. 1. These quantities are averages based on triplicate samples. The p24 concentrations were indistinguishable from background levels, which indicates that the zinc treatment completely abolished viral infectivity.

Figure 2:
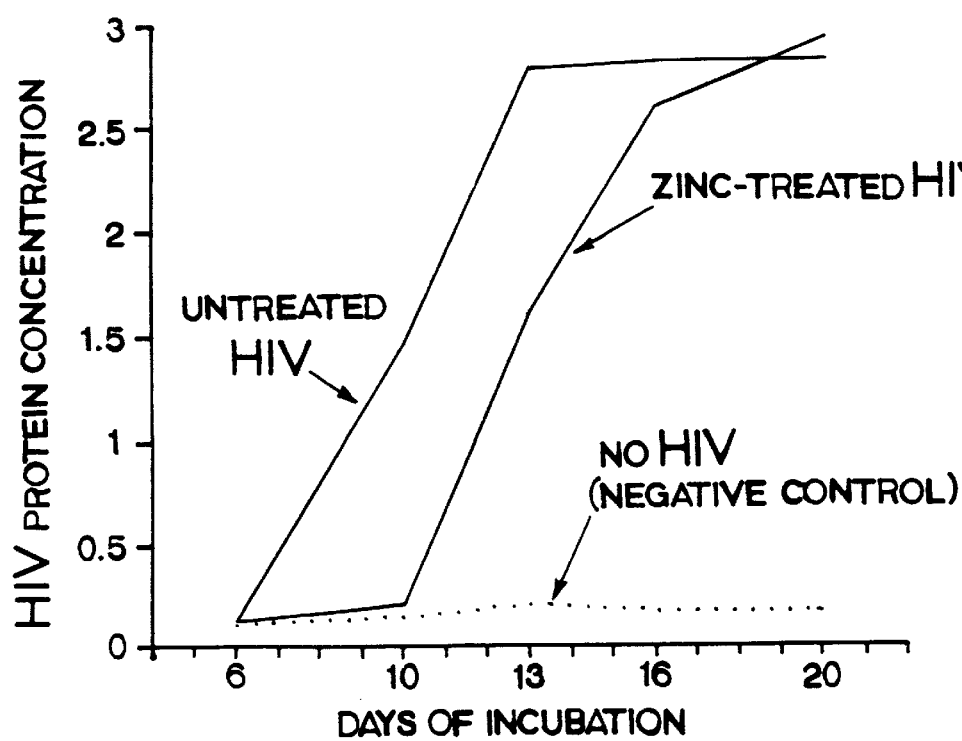
FIG. 2 shows that HIV infectivity was reduced and delayed when concentrated viral stocks were incubated with 1% zinc acetate for 2 hours before the zinc-virus solution was diluted (1:100) and mixed with lymphocytes.

Data from the 1:100 dilution test are shown in FIG. 2. One of the tubes became infected by mold after the 10th day, so subsequent values are based on averages from two samples. These results indicated that the zinc suppressed and retarded HIV infectivity; however, apparently, some small fraction of the viruses apparently remained infective.

EXAMPLE 9

DILUTED HIV INFECTIVITY TESTS

The tests described above, in Example 8, used an undiluted high-titer viral stock, which contained at least ten million infectious viral particles per ml. That concentration can be achieved in a laboratory only by special culturing, purification, and concentration techniques, and it is vastly higher than would actually occur in the ejaculate of an HIV-infected person (especially someone who is not in the end stages of the disease, and who might pose a significant risk of transmitting the virus to an unknowing sexual partner).

In a subsequent series of tests, ZnAc was tested against diluted viral stocks; in these tests, the zinc completely eliminated the infectivity of the infected viruses. These tests used serial dilutions of the viral stocks, at ranges from 1:10 to 1:10,000. To create the 1:10 dilution, 500 µl of viral stock was mixed with 4.5 ml of RPMI medium. Subsequent dilutions added 9 ml of RPMI medium to 1 ml from the preceding dilution.

A 2 ml aliquot from each dilution was mixed with an equal volume of 3% ZnAc dissolved in sterile distilled water; after mixing, the zinc concentration was 5.3 mg/ml Zn. These mixtures were incubated for 2 hours, then diluted with culture medium at 1:30, 1:100, and 1:1000 to reduce the toxicity of the zinc to lymphocytes. Four ml of lymphocytes were mixed with 4 ml of each zinc/virus mixture. The zinc/virus/cell mixtures were incubated at 37° C. for 3 hours; zinc concentrations were 88, 27, and 2.7 µg/ml in the 30, 100, and 1000 dilutions. During subsequent culturing, significant cell mortality was observed in the 88 µg/ml treatment batch, but no cell mortality was observed at the lower levels.

Following the 3 hour incubation, the cells were washed twice in RPMI medium and resuspended in fresh medium containing 10% FCS. Each solution was inoculated (2 ml; estimated minimum $2 \times 10^5$ cells per well) into each of three wells in a 12-well plate and cultured for 27 days, with periodic sampling and measuring of p24 antigens.

Figure 3:
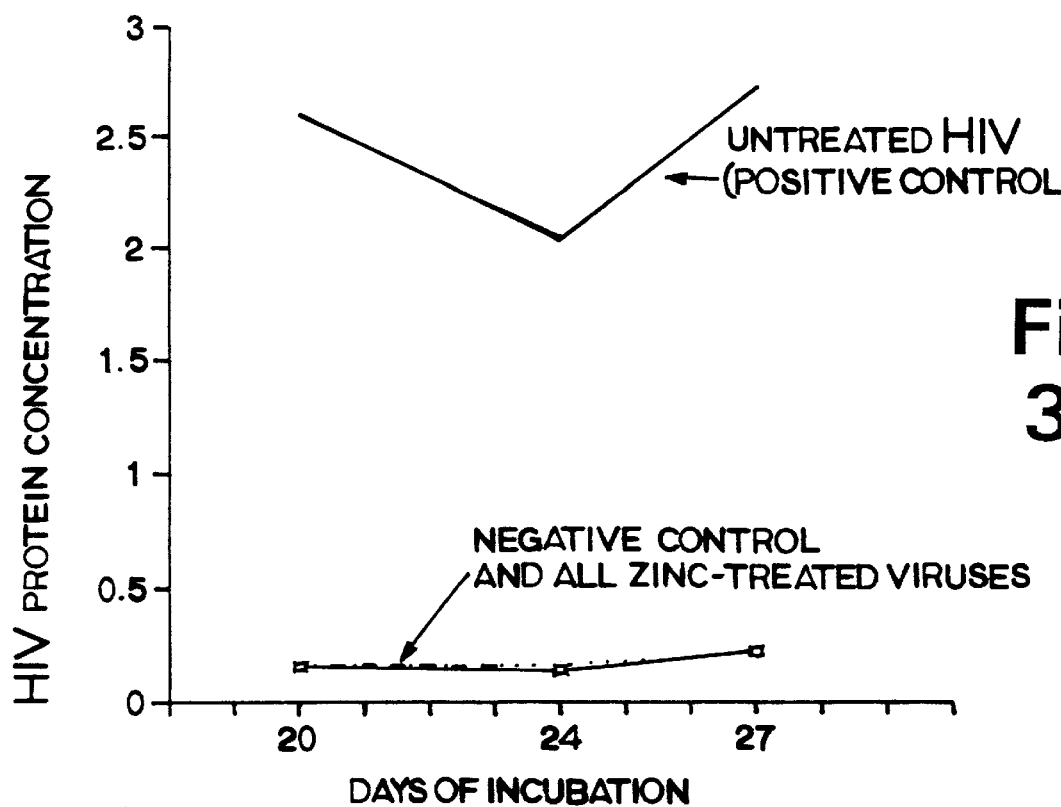
FIG. 3 shows that HIV infectivity was completely eliminated when various dilutions of high-titer viral stocks were incubated with 1.5% zinc acetate for 2 hours.

ELISA data for the 10×, 100×, and 1000× high-titer viral stock dilutions, treated with the 1000× dilution of the zinc/virus mixture (2.7 µg/ml Zn final concentration) are shown in FIG. 3. As shown, the zinc treatment completely blocked infectivity. Data for the diluted viral stocks treated with 1:100 zinc/virus dilutions (27 µg/ml Zn) were virtually identical, and viral infectivity was completely blocked.

Negative controls were identically diluted cells that did not contain zinc or HIV. Positive controls used 1:1000 dilutions of viral stock mixed with zinc-free RPMI. These controls were consistently highly infectious, even though their concentrations were 100× lower than the 1:10 mixtures in which infectivity was eliminated by zinc treatment. Other positive controls were tested at up to 100,000× dilutions; these were highly infective in two out of the three plates tested.

Figure 4:
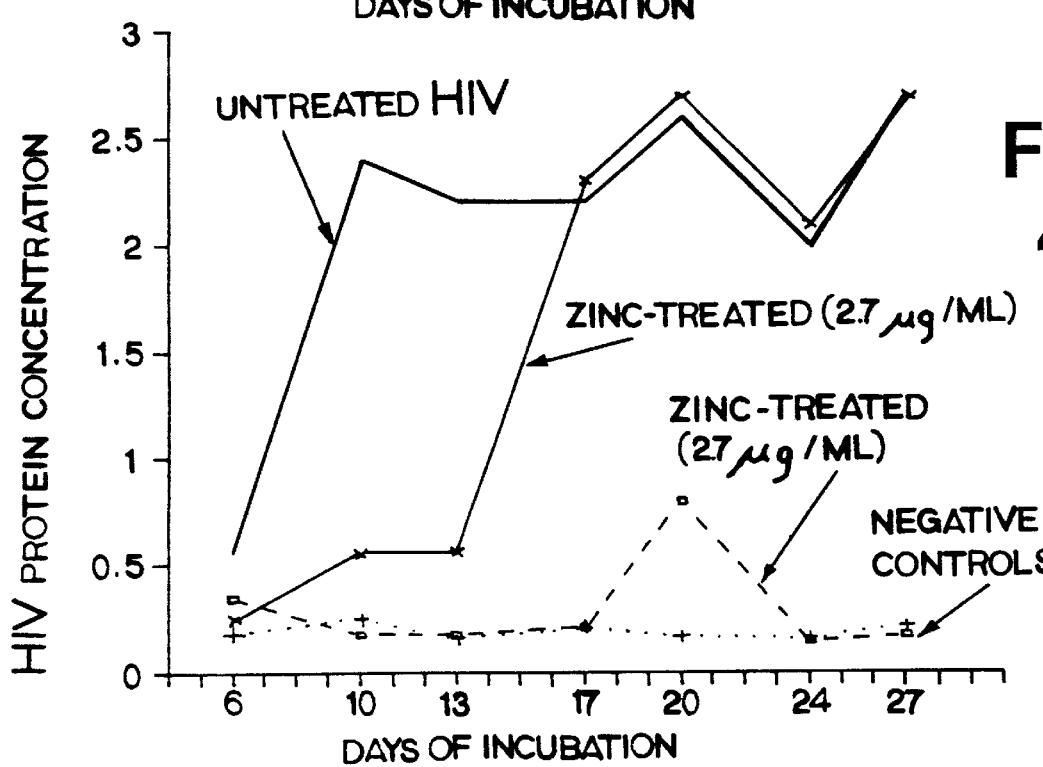
FIG. 4 shows that HIV infectivity was either eliminated or suppressed when high-titer viral stocks were incubated with various concentrations of zinc acetate.

While carrying out the viral dilution tests, tests were also performed using 2 ml of 3% ZnAc solution in distilled water mixed with 2 ml aliquots of undiluted viral stock. The zinc/virus mixtures were incubated for 2 hours, diluted with RPMI at 1:100 and 1:1000 ratios, and mixed with lymphocytes for three hours; zinc concentrations were 27 and 2.7 µg/ml. The cells were washed twice, inoculated into 12 well plates as described above, and cultured for 27 days. ELISA results are shown in FIG. 4. As shown, the 1:100 dilution (27 µg/ml Zn) completely prevented infectivity, while the 1:1000 dilution (2.7 µg/ml) delayed the onset of infection.

EXAMPLE 10

HIV PRECIPITATION TESTS

Precipitation tests using HIV were also carried out Biotech Research Laboratories, using 2% ZnAc which was mixed with an equal volume of undiluted viral stock, incubated for 24 hours, and centrifuged at 1500 rpm in a tabletop centrifuge for 5 minutes. The supernatant was sampled (100 µl) and serially diluted by medium, at 1:10 followed by 2× dilutions (1:20, 1:40, 1:80, etc) to a maximum dilution of 1:10240. Each dilution was analyzed spectrophotometrically to determine the concentration of viruses suspended in solution. After sampling, each tube was hand-mixed and incubated for 24 hours. The solution near the top of the tube was sampled again, serially diluted, and tested using the ELISA assay. The tube was hand-mixed again, incubated for three more days, and sampled again to obtain Day 5 values.

The values for zinc-treated viruses averaged about 40% less than values for identically diluted solutions that did not receive zinc treatment. This indicates that the zinc caused substantial precipitation of the virus and lowered the concentration of free HIV particles in solution.

EXAMPLE 11

ANTI-VIRAL TESTS USING HERPES VIRUSES

After the HIV tests described above had been completed, the Applicant contracted with a viral research laboratory at a university to study herpes viruses, which are much easier, faster, cheaper, and safer to work with than HIV. Several strains of herpes simplex virus (HSV) were tested, using standardized plaque assays; all showed comparable inhibition by the zinc salts that were tested. Several cells lines were also tested; all cell lines showed comparable levels of zinc toxicity, which typically began to appear in mild form at roughly 100 mM for zinc acetate and about 200 mM for zinc lactate or gluconate. After those toxicity tests had been evaluated, the viral inhibition tests were done on CV-1 cells, an immortalized cell line originally from a monkey kidney, which is highly and reliably susceptible to herpes virus infection, and which is widely used in in vitro tests on herpes viruses.

The initial virus-plus-zinc incubation step using HSV and CV-1 cells was tested at various durations, ranging from 2 hours down to 5 minutes, using constant 50 mM zinc salt concentrations (most tests were done with zinc gluconate or zinc lactate). The results showed 100% virus inhibition for all incubation times of 15 minutes or greater, and 98 to 99% inhibition levels at 5 minutes incubation time.

Tests were also carried out using a range of zinc salt concentrations, from 50 mM down to 5 mM, using constant 2 hour incubation periods. All concentrations of 30 mM or higher showed 100% viral inhibition; 15 mM zinc concentrations showed 98 to 99% virus inhibition, and 5 mM zinc concentrations showed 63 to 86% virus inhibition.

All of these results clearly confirm that zinc salts dissolved in water are effective in reducing the infectivity of herpes viruses.

It also should be kept in mind that the concentrations of zinc used in the HSV tests were measured in millimolar quantities. For example, a 30 mM zinc salt concentration (which inhibited viruses at the 100% level in the HSV tests described above) translates to 50/1000 of a mole of zinc per liter, or about 50 millionths of a mole of zinc (about 0.002 grams of zinc) per cubic centimeter. By comparison, zinc contents in genital lubricants can be measured as percentages, rather than in millimolar quantities. A lubricant containing 5% percent w/v of a zinc salt (this is an entirely feasible level, which has been shown to cause no genital irritation) will contain about 10 times as much zinc as the 30 mM level that inhibited viruses at the 100% level in the HSV tests described above.

Thus, there has been shown and described a composition and method for reducing the risk of infection by sexually transmitted viruses. Although this invention has been exemplified for purposes of description and illustration by reference to certain specific embodiments, it will be apparent to those skilled in the art that various modifications and alterations of the illustrated examples are possible. Any such equivalents which derive directly from the teachings herein, and which do not depart from the spirit and scope of the invention, are deemed to be covered by this invention.

REFERENCES

Cannan, R. K., and Kibrick, A., "Complex formation between carboxylic acids and divalent metal cations," *J. Amer. Chem. Soc.* 60: 2314 (1938)

Eliasson, R. and Lindholmer, C., "Zinc in human seminal plasma," *Andrology* 3: 147 (1971)

Eliasson, R., "Effect of zinc on human sperm respiration," *Life Science* 10: 1317 (1971)

Fair, W. R., et al, "Prostatic antibacterial factor, identity and significance," *Urology* 7: 169–177 (1976)

Firpo, E. J., and E. L. Palma, "Inhibition of foot and mouth disease virus and procapsid synthesis by zinc ions," *Arch. Virol.* 61: 175–181 (1979)

Fridlender, B., et al, "Selective inhibition of herpes simplex virus type 1 DNA polymerase by zinc ions," *Virology* 84: 551–554 (1978)

Griessar, R., et al, *Inorg. Nuclear Chem. Letters* 4: 443 (1968)

Gupta, P. and Rapp, F., "Effect of zinc ions on synthesis of herpes simplex virus type 2-induced polypeptides," *Proc. Soc. Exp. Biol. and Med.* 152: 455–458 (1976)

Homonnai, Z. T., et al, "Prolactin and zinc in the human ejaculate," *Andrologia* 10: 66 (1978)

Korant, B. D. and B. E. Butterworth, "Inhibition by zinc of rhinovirus protein cleavage: interaction of zinc with capsid polypeptides," *J. Virol.* 18: 298–306 (1976)

Lide, D. R., ed., *CRC Handbook of Chemistry and Physics*, 71st Edition (Boca Raton, Fla., 1990)

Linke, W. F., ed., *Solubility of Inorganic and Metal Organic Compounds*, 4th Edition Marmar, J. L., "Values for zinc in whole semen, fractions of split ejaculate, and expressed prostatic fluid," *Urology* 16: 478–480 (1980)

Merluzzi, V. J., et al, "Evaluation of zinc complexes on the replication of rhinovirus 2 in vitro," *Res. Commun. Chem. Pathol. Pharmacol.* 66: 425–440 (1989)

Novick, S. G., et al, "How does zinc modify the common cold? Clinical observations and implications regarding mechanisms of action," *Medical Hypotheses* 46: 295–302 (1996)

Paz, G., "Human semen analysis," *Int. J. Fertil.* 22: 140 (1977)

Pearce-Pratt, R. and Phillips, D. M., "Studies of adhesion of lymphocytic cells: Implications for sexual transmission of HIV," *Biol. of Reproduction* 48: 431–445 (1993)

Phillips, D. M. and Bourinbaiar, A. S., "Mechanism of HIV spread from lymphocytes to epithelia," *Virology* 186: 261–273 (1992)

Shlomai, J., Asher, Y., Gordon, Y. J., Olshevsky, U., and Becker, Y., "Effect of zinc ions on the synthesis of herpes simplex virus DNA in infected BSC-1 cells," *Virology* 66: 330–335 (1975)

Sillen, L. G., and Martell, A. E., *Stability Constants of Metal Ion Complexes*, Special Publication No. 17 (The Chemical Society, London, 1964)

Sillen, L. G., and Martell, A. E., *Stability Constants of Metal Ion Complexes*, Special Publication No. 25 (The Chemical Society, London, 1971)

Vallee, B. I. and Falchuk, K. H., "The biochemical basis of zinc physiology," *Physiological Reviews* 73: 79–118 (1993)

Weislow, O. S., et al, "New soluble-formazan assay for HIV-1 cytopathic effects: Application to high-flux screening of synthetic and natural products for AIDS-antiviral activity," *J. Natl. Cancer Inst.* 81: 577–586 (1989)

Zacharopoulos, V. A., et al, "Lymphocyte-facilitated infection of epithelia by HTLV Type I," *J. Virology* 66: 4601–4605 (1992)

Zaslavsky, V., "Inhibition of vaccinia virus growth by zinc ions: effects on early RNA and thymidine kinase synthesis," *J. Virology* 29: 405–408 (1979)

I claim:

1. An article of manufacture comprising a watertight container and a genital lubricant contained therein, wherein the genital lubricant comprises at least one zinc salt which, when dissolved in aqueous solution, releases zinc ions at a concentration effective to reduce the infectivity of at least one type of sexually transmitted virus, and wherein the genital lubricant is physiologically acceptable for repeated use as a lubricant during sexual intercourse.

2. The article of manufacture of claim 1 wherein the sexually transmitted virus is selected from the group consisting of herpes simplex viruses, human immunodeficiency viruses, hepatitis viruses, and papilloma viruses.

3. The article of manufacture of claim 1 wherein the zinc salt is selected from the group consisting of zinc acetate, zinc butyrate, zinc formate, zinc gallate, zinc gluconate, zinc glycerate, zinc glycolate, zinc lactate, zinc maleate, zinc malonate, zinc propionate, zinc pyruvate, zinc succinate, zinc chloride, and zinc sulfate.

4. The article of manufacture of claim 3 wherein the zinc salt is selected from the group consisting of zinc acetate, zinc gluconate, zinc lactate, and zinc propionate.

5. The article of manufacture of claim 3 wherein the zinc salt is selected from the group consisting of zinc chloride and zinc sulfate.

6. The article of manufacture of claim 1 wherein the watertight container comprises a watertight tube made of deformable material, sealed at a first end and having an outlet orifice at an opposed second end.

7. The article of manufacture of claim 6 wherein the deformable material comprises at least one deformable plastic wall.

8. The article of manufacture of claim 6 wherein the deformable material comprises metallic foil.

9. The article of manufacture of claim 1 wherein the watertight container comprises a sealed watertight package which can be opened by tearing or breaking, and which contains at least a single application amount of the genital lubricant.

10. The article of manufacture of claim 1 wherein the watertight container comprises a stiff-walled bottle with a dispenser device.

11. The article of manufacture of claim 1 wherein the watertight container comprises a vaginal insertion device.

* * * * *